(12) United States Patent
Choi et al.

(10) Patent No.: US 9,874,811 B2
(45) Date of Patent: Jan. 23, 2018

(54) PHOTOPOLYMER COMPOSITION FOR HOLOGRAPHIC RECORDING

(71) Applicant: SAMSUNG ELECTRONICS CO., LTD., Suwon-si (KR)

(72) Inventors: Chilsung Choi, Suwon-si (KR); Evgeny V. Vasiliev, Novosibirsk (RU); Vladimir V. Shelkovnikov, Novosibirsk (RU); Vladimir Loskutov, Novosibirsk (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/260,839

(22) Filed: Sep. 9, 2016

(65) Prior Publication Data

US 2017/0075214 A1  Mar. 16, 2017

(30) Foreign Application Priority Data

Sep. 10, 2015  (KR) .................. 10-2015-0128567
Aug. 3, 2016  (KR) .................. 10-2016-0099066

(51) Int. Cl.
*G03H 1/02* (2006.01)
*G03F 7/027* (2006.01)
(Continued)

(52) U.S. Cl.
CPC ............ *G03F 7/001* (2013.01); *C07C 381/12* (2013.01); *C09B 5/18* (2013.01); *C09B 5/40* (2013.01); *G02B 1/14* (2015.01); *G03F 7/0045* (2013.01); *G03F 7/027* (2013.01); *G03F 7/033* (2013.01); *G03F 7/038* (2013.01); *G03F 7/11* (2013.01); *G03H 1/02* (2013.01); *G03H 1/0256* (2013.01); *G03H 2001/0264* (2013.01)

(58) Field of Classification Search
None
See application file for complete search history.

(56) References Cited

U.S. PATENT DOCUMENTS 3,769,336 A * 10/1973 Lee .................... C08F 20/20
560/217
3,774,305 A * 11/1973 Stoffey .................. C08F 20/20
433/228.1

(Continued)

FOREIGN PATENT DOCUMENTS

JP  10-212286 A  8/1998
WO  02/44258 A2  6/2002
(Continued)

OTHER PUBLICATIONS

Shelkovnokov et al., "Spectral sensitization sulfonium salts covalently bonded to Keramidaninovymi dyes in holographic recording in photopolymer material", Presentation at 11th international conference HOLOEXPO—2014, Sochi, Russia, (Sep. 16-17, 2014) (program attached 14 pages).*

(Continued)

*Primary Examiner* — Martin Angebranndt
(74) *Attorney, Agent, or Firm* — Sughrue Mion, PLLC

(57) ABSTRACT

Provided is a photopolymer composition that may exhibit low volume shrinkage during holographic recording and may prevent a photosensitive dye from remaining unbleached after holographic recording.

14 Claims, 4 Drawing Sheets

(51) Int. Cl.
| | |
|---|---|
| G03F 7/029 | (2006.01) |
| G03F 7/004 | (2006.01) |
| G03F 7/11 | (2006.01) |
| C09B 5/18 | (2006.01) |
| C09B 5/40 | (2006.01) |
| C07C 381/12 | (2006.01) |
| G03F 7/00 | (2006.01) |
| G03F 7/033 | (2006.01) |
| G02B 1/14 | (2015.01) |
| G03F 7/038 | (2006.01) |

(56) References Cited

U.S. PATENT DOCUMENTS

| | | | | |
|---|---|---|---|---|
| 3,819,665 | A * | 6/1974 | Bosshard | C09B 1/60 544/294 |
| 3,876,664 | A * | 4/1975 | Bosshard | C09B 1/60 549/13 |
| 8,298,726 | B2 * | 10/2012 | Shimizu | G03H 1/02 359/3 |
| 2005/0259216 | A1 * | 11/2005 | Lin | G02F 1/13342 349/196 |
| 2006/0003261 | A1 * | 1/2006 | Imai | C08F 22/105 430/288.1 |
| 2007/0092804 | A1 | 4/2007 | Kolb et al. | |
| 2014/0127611 | A1 | 5/2014 | Choi et al. | |
| 2014/0349218 | A1 * | 11/2014 | Shimizu | G11B 7/245 430/2 |

FOREIGN PATENT DOCUMENTS

| | | |
|---|---|---|
| WO | 03/002557 A1 | 1/2003 |
| WO | 03/072567 A1 | 9/2003 |
| WO | 03/072568 A1 | 9/2003 |
| WO | 2011/082488 A1 | 7/2011 |

OTHER PUBLICATIONS

Podkoscielna "The influence of oxidation number of sulfur on the polymerization and thermo-mechanical properties of dimethacrylate co-polymers", J. Therm. Anal. Chem., vol. 111 pp. 1553-1560 (Jul. 2012).*
Shelkovnikov et al. Synthesis and thermomechanical properties of hybrid photopolymer films based upon the thiol-siloxane and acrylate oligomers, J Mater. Sci., vol. 50 pp. 7544-7556 (Aug. 2015).*
Jinxin Guo et al; "A Review of the Optimisation of Photopolymer Materials for Holographic Data Storage"; Physics Research International; 2012; 17 pgs. total.
Michael R. Gleeson et al; "Comparison of a new self developing photopolymer with AA/PVA based photopolymer utilizing the NPDD model"; Optics Express; vol. 19; No. 27; Dec. 19, 2011; 18 pgs. total.
"CROP photopolymers for hologram recording"; Holography SPIE's International Technical Group Newsletter; vol. 11; No. 2; Dec. 2000; 12 pgs. total.
Chunhe Zhao et al; "Shrinkage correction of volume phase holograms for optical interconnets"; SPIE; vol. 3005; Apr. 4, 1997; 6 pgs. total.
I Sh Steinberg et al; "Multilayer two-photon recording of microholograms in cationic ring-opening polymerization material"; Journal of Optics; vol. 15; 2013; 7 pgs. total.
V.V. Shelkovnikov et al; "New acid photogenerators based on thioxanthen-9-one sulfonium derivatives for detritylation in the oligonucleotide synthesis"; Russian Chemical Bulletin, International Edition; vol. 60; No. 3; pp. 561-569; 9 pgs. total.
D.A. Waldman et al; "CROP holographic storage media for optical data storage at greater than 100 bits/$\mu m^2$"; Proceedings of SPIE; vol. 5216; 2003; pp. 10-25; 16 pgs. total.
R. Castagna et al; "Novel blue sensitive polymeric materials for optical data storage"; Proceedings of SPIE; vol. 7053; 2008; 8 pgs. total.
Ayman M Atta et al; "Synthesis of bisphenol a novolac epoxy resins for coating applications"; Journal of Applied Polymer Science; vol. 107; pp. 347-354; 9 pgs. total.
Daohong Zhang et al; "Bisphenol-A epoxy resin reinforced and toughened by hyperbranched epoxy resin"; Front. Chem. Eng. China; vol. 1; No. 4; 2007; pp. 349-354; 6 pgs. total.
Beata Podkoscielna et al; "Synthesis, characterization, and thermal properties of diacrylic/divinylbenzene copolymers"; J Therm Anal Calorim; 2010; pp. 235-241; 7 pgs. total.
William K. Smothers et al; "Photopolymers for holography"; SPIE; vol. 1212; Practical Holography IV; 1990; pp. 20-29; 10 pgs. total.
J.T. Gallo et al; "Model for the effects of material shrinkage on volume holograms"; Applied Optics; vol. 33; No. 29; Oct. 10, 1994; pp. 6797-6804; 8 pgs. total.
Sylvia H. Stevenson et al; "A Method for Characterization of Film Thickness and Refractive Index in Volume Holographic Materials"; SPIE; vol. 2405; pp. 88-97; 10 pgs. total.
Mohesh Moothanchery et al; "Study of the Shrinkage caused by holographic grating formation in acrylamide based photopolymer film"; Optics Express; vol. 19; No. 14; Jul. 4, 2011; pp. 13395-13404; 10 pgs. total.
Pavel Trochtchanovitch et al; "Method of characterization of effective shrinkage in reflection holograms"; Opt. Eng.; vol. 43; No. 5; May 2004; pp. 1160-1168; 9 pgs. total.
M. Moothanchery et al; "Real time shrinkage studies in photopolymer films using holographic interferometry"; Proc. of SPIE; vol. 8437; pp. 843701-1-843701-6; 6 pgs. total.
D.A. Waidman et al; "Determination of low transverse shrinkage in slant fringe gratings of a cationic ring-opening volume hologram recording material"; Invited Paper; SPIE; vol. 3010; pp. 354-372; 19 pgs. total.
Gene Campbell et al; Comparison of methods for determining the bias index of a dichromated gelatin hologram; Applied Optics; vol. 34; No. 14; May 10, 1995; pp. 2548-2555; 8 pgs. total.
H.D. Tholl et al; "Determination of the mean refractive index and the thickness of dichromated gelatin holographic films using the thin film resonance method"; SPIE; vol. 2405; pp. 76-87; 12 pgs. total.
E.F. Pen et al; "A method for research of dynamics of the spectral characteristics of reflection holograms in photopolymer materials"; Proceedings of SPIE; vol. 4900; 2002; pp. 957-961; 5 pgs. total.
S.A. Babin et al; "Methods and Devies for Holographic Photopolymer Material Testing"; Optoelectronics Instrumentation and Data Processing; vol. 39; No. 2; 2003; pp. 49-59; 11 pgs. total.

* cited by examiner

PHOTOPOLYMER COMPOSITION FOR HOLOGRAPHIC RECORDING

CROSS-REFERENCE TO RELATED APPLICATION

This application claims priority from Korean Patent Application No. 10-2015-0128567, filed on Sep. 10, 2015, and Korean Patent Application No. 10-2016-0099066, filed on Aug. 3, 2016, in the Korean Intellectual Property Office, the disclosures of which are incorporated by reference herein in their entireties.

BACKGROUND

1. Field

The present disclosure relates to photosensitive recording media, and more particularly, to a photopolymer composition for holographic recording, and a holographic recording medium using the photopolymer composition.

2. Description of the Related Art

Upon irradiation by a laser, monomers in a photopolymer composition for holographic recording form a polymer via polymerization. As a result, an interference pattern may be created in the photopolymer composition, and modulation of the refractive index may occur, such that a phase hologram having high diffraction efficiency may be formed.

Unlike silver halide and dichromated gelatin, which have been used as conventional materials for holographic recording, a photopolymer does not have their drawbacks. That is, using a photopolymer for recording holograms does not require a variety of post-processes, including a wet post-process, and enables recording of good quality holograms in real time. The wet post-process means a process wherein a holographic image is developed and fixed by means of a "liquid" developer and a "liquid" fixing agent. For example, the wet post-process may comprises: developing an holographic image by using a liquid developer; removing the liquid developer by means of washing with water; fixing the developed image by using a liquid fixing agent; removing the liquid fixing agent by means of washing with water; dipping the fixed image into a solution of an activating agent; and drying the fixed image.

However, a photopolymer composition may undergo volumetric shrinkage during the conversion of monomers into a polymer. This may result in the tilting of created gratings and a consequential change in diffraction efficiency.

In general, a photopolymer exhibits shrinkage of from about 1% to about 5%. For example, a Bayer Material-Science's photopolymer has a shrinkage of less than 1.1% (Optics Express, Vol. 19, Issue 27, pp. 26325-26342 (2011)), and a DUPONT photopolymer has shrinkage of from about 3% to 5.5% (SPIE VoL 3005-0277-786X/971). US 2007/0092804 A1 discloses a photopolymer having a low shrinkage of 0.2% obtained via cationic ring-opening polymerization. However, the photopolymer disclosed in US 2007/0092804 A1 requires a high sensitivity of 80 to 100 mJ/cm$^2$.

SUMMARY

One or more exemplary embodiments provide a photopolymer composition that may exhibit low volume shrinkage during holographic recording and may prevent a photosensitive dye from remaining unbleached after holographic recording.

Additional aspects will be set forth in part in the description which follows and, in part, will be apparent from the description, or may be learned by practice of the presented embodiments.

According to an aspect of an exemplary embodiment, a photopolymer composition for holographic recording includes a photosensitive dye, a co-initiator, a monomer, a cross-linkable monomer, a binder resin, and a solvent, wherein the monomer includes dihydroxydiphenylsulfide tetraacrylate (DDTA), dihydroxydiphenylsulfide diacrylate (DDDA), or a combination thereof.

According to an aspect of another exemplary embodiment, a photopolymer composition includes a photosensitive dye, a co-initiator, a monomer, a cross-linkable monomer, a binder resin, and a solvent, wherein the monomer includes dihydroxydiphenylsulfide dioxirane (DDDO), and the photosensitive dye includes a sulfonium derivative of ceramidonin.

According to an aspect of another exemplary embodiment, a photosensitive dye includes a sulfonium derivative of ceramidonin represented by:

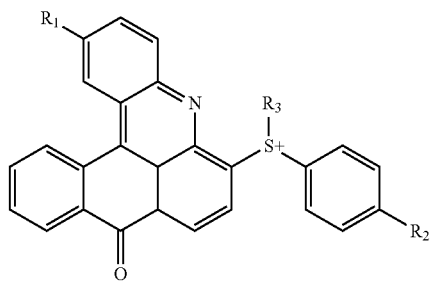

where $R_1$ and $R_2$ are each independently a hydrogen atom, a halogen atom, a $C_1$-$C_{10}$ alkyl group, a $C_1$-$C_{10}$ alkoxy group, or a primary or secondary amine group having a $C_1$-$C_{10}$ alkyl group; and $R_3$ is a $C_6$-$C_{12}$ aryl group or alkylaryl group.

According to an aspect of another exemplary embodiment, a photopolymer composition includes a photosensitive dye, a co-initiator, a monomer, a cross-linkable monomer, a binder resin, and a solvent, wherein the photosensitive dye includes a sulfonium derivative of ceramidonin represented by:

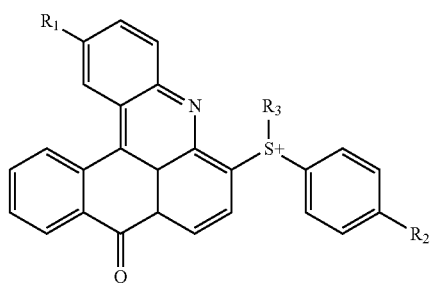

Where $R_1$ and $R_2$ are each independently a hydrogen atom, a halogen atom, a $C_1$-$C_{10}$ alkyl group, a $C_1$-$C_{10}$ alkoxy group, or a primary or secondary amine group having a $C_1$-$C_{10}$ alkyl group; and $R_3$ is a $C_6$-$C_{12}$ aryl group or alkylaryl group.

According to an aspect of another exemplary embodiment, a holographic recording medium includes a substrate, a photopolymer layer, and a protective layer, wherein the photopolymer layer is formed from any one of the above-described photopolymer compositions.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

Figure 1:
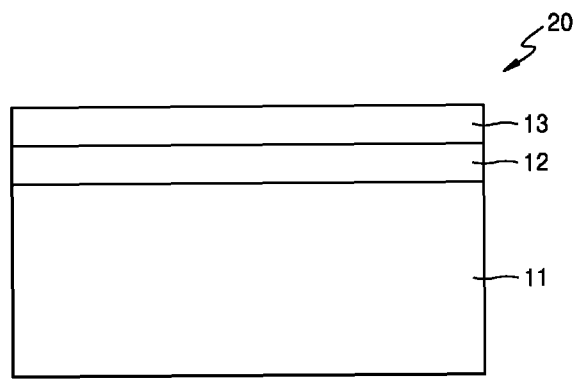
FIG. 1 is a schematic view of a holographic recording medium according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

According to a first exemplary embodiment, a photopolymer composition for holographic recording includes a photosensitive dye, a co-initiator, a monomer, a cross-linkable monomer, a binder resin, and a solvent, wherein the monomer includes dihydroxydiphenylsulfide tetraacrylate (DDTA), dihydroxydiphenylsulfide diacrylate (DDDA), dihydroxydiphenylsulfide dioxirane (DDDO), or a combination thereof.

The photosensitive dye may serve as a polymerization initiator of the monomer and the cross-linkable monomer by being stimulated upon irradiation of the photopolymer composition. For example, the photosensitive dye may include, but is not limited to, a sulfonium derivative of ceramidonin, new methylene blue, thioerythrosine triethylammonium, 6-acetylamino-2-methylceramidonin, eosin, erythrosine, rose bengal, thionine, basic yellow, pinacyanol chloride, Rhodamine 6G, gallocyanine, ethyl violet, Victoria blue R, celestine blue, quinaldine red, crystal violet, brilliant green, Astrazon orange G, Darrow red, Pyronin Y, Basic red 29, Pyrylium iodide I, Safranin O, cyanine, methylene blue, Azure A, or a combination thereof.

The co-initiator may facilitate the function of the photosensitive dye as an initiator. For example, an electron donor or an electron acceptor may be used as the co-initiator. Non-limiting examples of a suitable electron donor may include, but are not limited to, tetrabutylammonium butyltriphenylborate and 5-methyl-1,3,4-thiadiazole-2-thiol. A non-limiting example of a suitable electron acceptor is bis(4-tert-butylphenyl)iodine trifluoromethanesulfonate).

The monomer and the cross-linkable monomer may be the same or different to each other. The monomer may form a hologram pattern via polymerization. The monomer may include DDTA, DDDA, DDDO, or a combination thereof. When using cationic ring-opening polymerization (CROP) monomer such as DDDO, shrinkage during holographic recording may be partially compensated for by a volume increase resulting from the mechanism of the ring-opening polymerization. According to exemplary embodiments of the present disclosure, to suppress photopolymer shrinkage, a CROP monomer having a monoacrylate group or a branched acrylate group may be used. Such a CROP monomer may have an increased refractive index due to a sulfur atom in the molecular structure thereof.

DDDO may be represented by Formula 1.

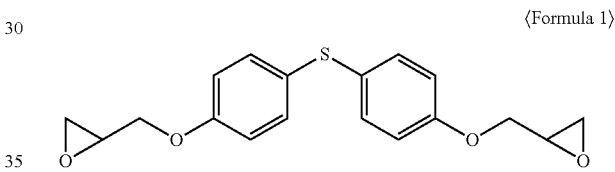

⟨Formula 1⟩

DDDO may have low shrinkage, high diffraction efficiency, and low sensitivity during polymerization. DDDO may be synthesized from, for example, dihydroxydiphenyl sulfide according to Reaction Scheme 1.

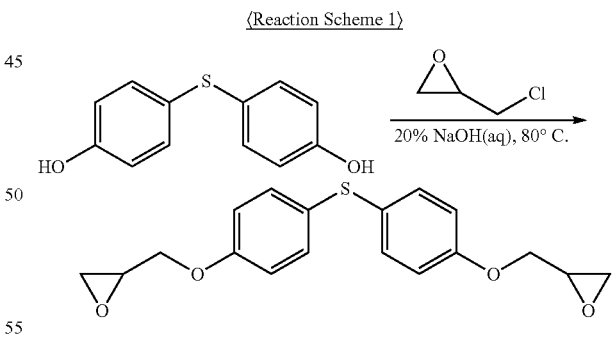

⟨Reaction Scheme 1⟩

DDDA may be represented by Formula 2.

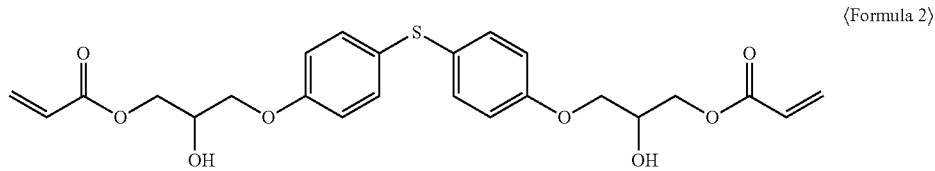 [SMILES: C=CC(=O)OCC(O)COc1ccc(Sc2ccc(OCC(O)COC(=O)C=C)cc2)cc1]

⟨Formula 2⟩

DDDA may have low shrinkage during polymerization, high diffraction efficiency, and low sensitivity. DDDA is disclosed in an article entitled "Synthesis, characterization, and thermal properties of diacrilic/divinylbenzene copolymers (Podkoscielna B. and Worzakowska M., J. Therm. Anal. Calorim. 2010, vol. 101, p. 235-241)," the entire contents of which are incorporated herein by reference. This article discloses a schematic process of synthesis with a phenolic starting material. The characteristics of DDDA may be analyzed using NMR $^{13}$C spectra and data from gas chromatography-mass spectroscopy (GC-MS). Synthesized DDDA may be considerably lost during washing, and thus may be used in the form of a mixed reaction product, not separated as a single compound. For example, DDDA may be synthesized from DDDO according to Reaction Scheme 2.

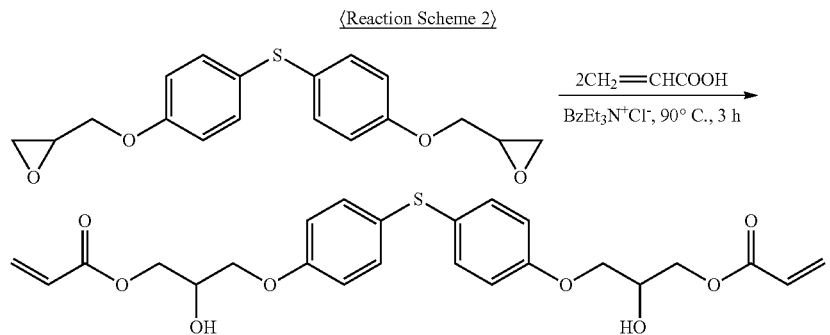

DDTA may be represented by Formula 3.

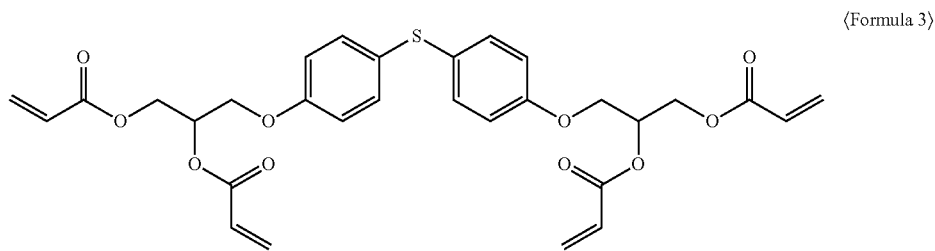 [SMILES: C=CC(=O)OCC(COc1ccc(Sc2ccc(OCC(COC(=O)C=C)OC(=O)C=C)cc2)cc1)OC(=O)C=C]

⟨Formula 3⟩

DDTA may have low shrinkage during polymerization, high diffraction efficiency, and low sensitivity. For example, DDTA may be synthesized from DDDA according to Reaction Scheme 3.

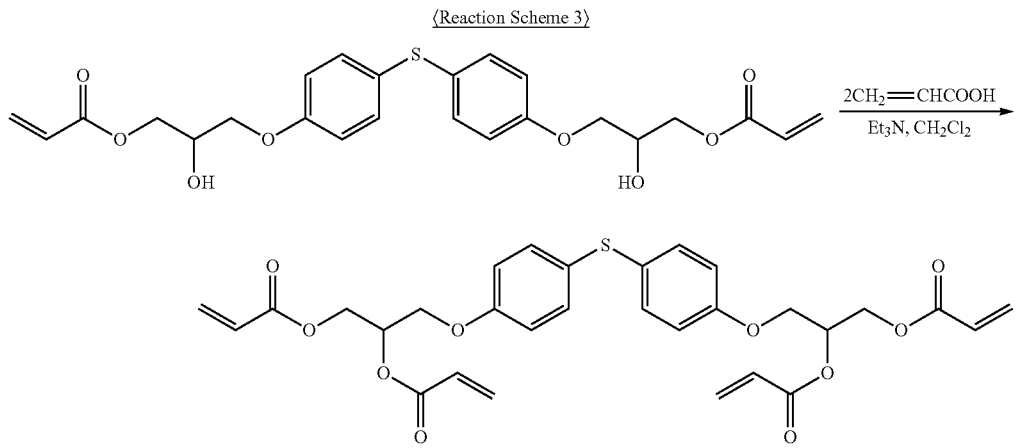

The cross-linkable monomer may form cross-linking bonds between polymer chains resulting from photopolymerization of the monomer. The cross-linking bonds may provide stability and rigidity to a recorded hologram and improve the lifespan of the hologram. Suitable cross-linkable monomers may include, but are not limited to, diacrylamide, triacrylamide, or a combination thereof. In addition, as the cross-linkable monomer, a 1,4-bis(acryloyl)piperazine derivative, a tris(acryloyl) 1,4,7-triazacyclononan derivative, or a combination thereof may be used.

The binder resin may ensure structural integrity of a photopolymer layer formed from the photopolymer composition. As an example, the binder resin may include, but is not limited to, polyvinylpyrrolidone, cellulose acetobutyrate, polyvinyl acetate, polyvinyl butyral, or a combination thereof.

The solvent may serve as a carrier for the photosensitive dye, the co-initiator, the monomer, the cross-linkable monomer, and/or the binder resin. As an example, the solvent may include, but is not limited to, chloroform, acetone, or a combination thereof.

For example, the photopolymer composition may include about 0.02 to about 0.03 wt % of the photosensitive dye, about 17 to about 19.5 wt % of the co-initiator, about 3.5 to about 15.9 wt % of the monomer, about 12 to about 13.8 wt % of the cross-linkable monomer, and about 55 to about 64 wt % of the binder resin, based on 100 wt % of a total weight of the photopolymer composition (in this aspect, the photopolymer composition being the photosensitive dye, the co-initiator, the monomer, the cross-linkable monomer, and the binder resin) excluding the solvent. As an example, the amount of the solvent may be about 100 to about 300 parts by weight based on 100 parts by weight of the total weight of the photopolymer composition excluding the solvent.

In some exemplary embodiments, the photosensitive dye of the photopolymer composition may include a sulfonium derivative of ceramidonin.

A triarylsulfonium salt is a conventional photoinitiator for polymerization of unsaturated compounds. As an example, the triarylsulfonium salt may include, but is not limited to, a sulfonium derivative of a sulfur-containing heterocyclic compound, such as thioxanthene, thianthrene, or benzothiophene. Such a conventional sulfonium photoinitiator has a drawback in that it absorbs only UV light. However, a sulfonium derivative of ceramidonin according to exemplary embodiments may absorb light having a longer wavelength that falls within the visible light spectrum. For example, the sulfonium derivative of ceramidonin may absorb light having a long wavelength of up to about 500 nm or greater at maximum. The sulfonium derivative of ceramidonin may also be bleached (or, decolored) within a reduced period of time after holographic recording.

The sulfonium derivative of ceramidonin according to an exemplary embodiment may be represented by Formula 4.

⟨Formula 4⟩

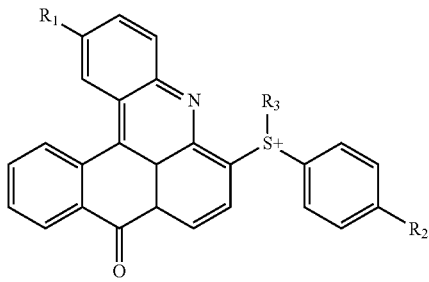

In Formula 4, $R_1$ and $R_2$ may each independently be a hydrogen atom, a halogen atom, a $C_1$-$C_{10}$ alkyl group, a $C_1$-$C_{10}$ alkoxy group, or a primary or secondary amine group having a $C_1$-$C_{10}$ alkyl group; and $R_3$ may be a $C_6$-$C_{12}$ aryl group or alkylaryl group. For example, $R_3$ may be a phenyl group or 4-tert-butyl-$C_6H_4$. However, exemplary embodiments are not limited thereto.

The sulfonium derivative of ceramidonin may be synthesized according to Reaction Scheme 4.

⟨Reaction Scheme 4⟩

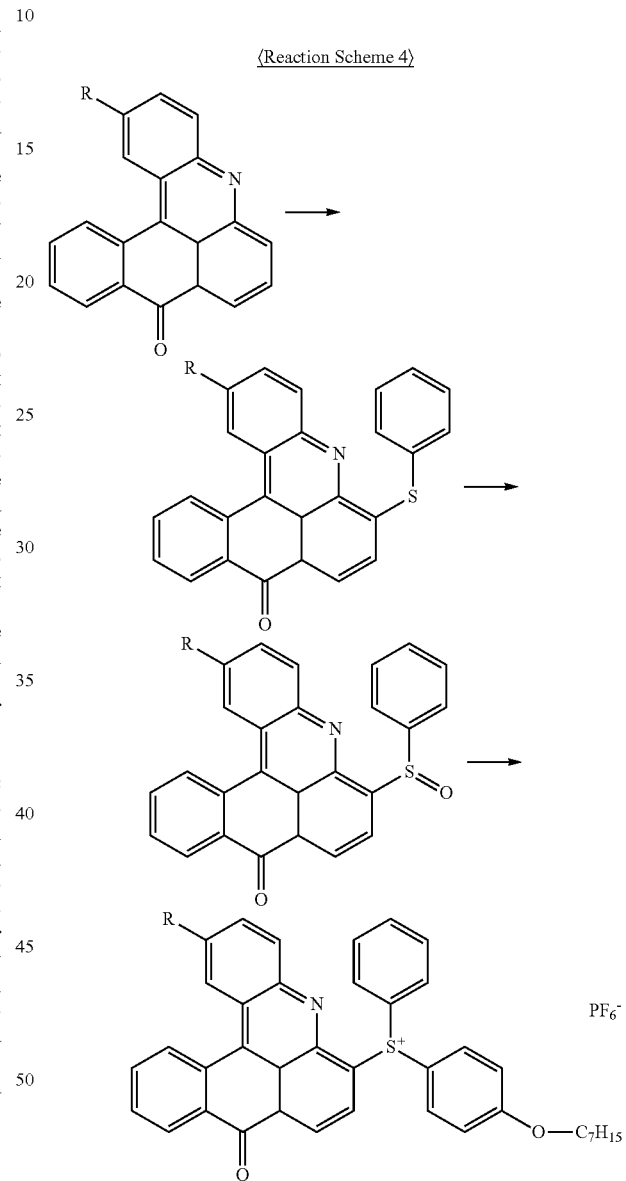

In some exemplary embodiments, the monomer of the photopolymer composition may include DDTA, and the photosensitive dye may include the sulfonium derivative of ceramidonin. In some other exemplary embodiments, the monomer of the photopolymer composition may include DDDA, and the photosensitive dye may include the sulfonium derivative of ceramidonin. In some other exemplary embodiments, the monomer of the photopolymer composition may include DDDO, and the photosensitive dye may include the sulfonium derivative of ceramidonin.

According to a second exemplary embodiment, a photopolymer composition for holographic recording includes a photosensitive dye, a co-initiator, a monomer, a cross-linkable monomer, a binder resin, and a solvent, wherein the monomer includes DDDO, and the photosensitive dye includes a sulfonium derivative of ceramidonin. In some exemplary embodiments, the monomer may further include DDTA, DDDA, or a combination thereof. DDDA, DDTA, and DDDO, which may be synthesized as described above, may have the same sulfur-containing aromatic backbone, i.e., bis(4-hydroxyphenyl) sulfide. Therefore, DDDA and DDTA as a free radical monomer may have good compatibility with DDDO as a CROP monomer.

According to a third exemplary embodiment, there is provided a photosensitive dye including a sulfonium derivative of ceramidonin represented by Formula 4.

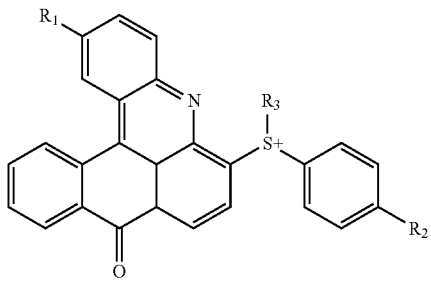

⟨Formula 4⟩

In Formula 4, $R_1$ and $R_2$ may each independently be a hydrogen atom, a halogen atom, a $C_1$-$C_{10}$ alkyl group, a $C_1$-$C_{10}$ alkoxy group, or a primary or secondary amine group having a $C_1$-$C_{10}$ alkyl group; and $R_3$ may be a $C_6$-$C_{12}$ aryl group or alkylaryl group. For example, $R_3$ may be a phenyl group or 4-tert-butyl-$C_6H_4$. However, exemplary embodiments are not limited thereto.

According to a fourth exemplary embodiment, a photopolymer composition for holographic recording includes a photosensitive dye, a co-initiator, a monomer, a cross-linkable monomer, a binder resin, and a solvent, wherein the photosensitive dye includes a sulfonium derivative of ceramidonin represented by Formula 4.

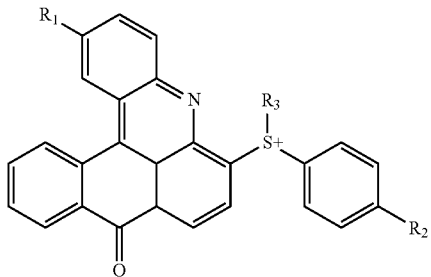

⟨Formula 4⟩

In Formula 4, $R_1$ and $R_2$ may each independently be a hydrogen atom, a halogen atom, a $C_1$-$C_{10}$ alkyl group, a $C_1$-$C_{10}$ alkoxy group, or a primary or secondary amine group having a $C_1$-$C_{10}$ alkyl group; and $R_3$ may be a $C_6$-$C_{12}$ aryl group or alkylaryl group. For example, $R_3$ may be a phenyl group or 4-tert-butyl-$C_6H_4$. However, exemplary embodiments are not limited thereto.

For example, the monomer may be DDTA, DDDA, DDDO, N-acryloylthiomorpholine, or a combination thereof. However, exemplary embodiments are not limited thereto.

Details of the other components of the photopolymer composition may be the same as those described above with reference to the photopolymer composition for holographic recording according to the first exemplary embodiment.

According to a fifth exemplary embodiment, there is provided a holographic recording medium including a substrate, a photopolymer layer, and a protective layer.

FIG. 1 is a schematic view of a holographic recording medium 20 according to an exemplary embodiment of the present disclosure. Referring to FIG. 1, the holographic recording medium 20 may include a substrate 11, a photopolymer layer 12, and a protective layer 13.

The substrate 11 may be formed from transparent glass or plastic. When the substrate 11 is a plastic substrate, the substrate 11 may be formed from polycarbonate (PC), polyethylene terephthalate (PET), polybutylene terephthalate, polyethylene, polypropylene, cellulose acetate, cellulose nitrate, polystyrene, polyepoxide, polysulfone, cellulose triacetate (CTA), polyamide, polymethylmethacrylate, polyvinyl chloride, polyvinyl butyral, polydicyclopentadiene, or a combination thereof.

The photopolymer layer 12 may be on the substrate 11. The photopolymer layer may be formed directly on the substrate, with no other material present between the two layers. The photopolymer layer 12 may be formed by coating a photopolymer composition according to any of the above-described exemplary embodiments on the substrate 11. The photopolymer layer 12 may have a thickness of about 10 to about 100 μm, or, in some exemplary embodiments, about 20 to about 80 μm, or, in some other exemplary embodiments, about 30 to about 50 μm.

The protective layer 13 may be on the photopolymer layer 12. The protective layer may be formed directly on the photopolymer layer, with no other material present between the two layers. The protective layer 13 may protect the photopolymer layer 12 from oxygen during holographic recording and from other mechanical and environmental influences. The protective layer may be any suitable protective layer known in the art. As an example, the protective layer 13 may include a polyethylene film.

One or more exemplary embodiments of the present disclosure will now be described in detail with reference to the following examples. However, these examples are for illustrative purposes only and do not limit the scope of the exemplary embodiments of the present disclosure.

EXAMPLE

Synthesis Example 1: DDDO Monomer 22 mL (26 g, 0.28 mol) of epichlorohydrin was added dropwise to a mixed solution including 50 mL of a 20 wt % aqueous solution of sodium hydroxide and 10 g (0.046 mol) of 4,4'-dihydroxy diphenyl sulfide, at 50° C. for 1 hour. The resulting reaction mixture was heated to 80° C. and stirred for 3 hours. After the reaction mixture was cooled down to room temperature (25° C.), 50 mL of methylene chloride was added thereto to allow an organic phase to be separated. The separated organic phase was washed with water and dried with $CaCl_2$, and then evaporation was performed with a vacuum rotary evaporator to remove the solvent. The resulting residue (colorless oil) was dissolved in benzene and purified by column chromatography (stationary phase: $SiO_2$ (50-160 mcm), eluent: benzene). The resulting product was a low-melting point solid compound, and the yield was 9.7 g (64%). The resulting product had the same nuclear magnetic resonance (NMR) spectra as those of oxirane. $^1$H NMR spectra with chemical shifts (δ) in ppm were recorded using the signals of the residual protons of $CHCl_3$ (δH=7.24 ppm) in deuterochloroform ($CDCl_3$) on a Bruker AM-400 spectrometer ($^1H$: 400.13 MHz) with tetramethylsilane (TMS) as internal standard. [1H NMR, δ (J, Hz): 2.73 (dd, 1H, CH2, J1=4.9, J2=2.7), 2.88 (dd, 1H, CH2, J1=4.9, J2=4.2), 3.32 (m, 1H, CH), 3.90 (dd, 1H, CH2, J1=11.2, J2=5.7), 4.18 (dd, 1H, CH2, J1=11.2, J2=3.2), 6.84, 7.25 (Aft each on 2Harom, J=8.9) HRMS: calc. for C18H18O4S [M+]: 330.0920; found: m/z 330.0927].

Synthesis Example 2: DDDA Monomer 10 g (30 mmol) of 2-(4{[4-(oxyran-2-yl-methoxy)phenyl]-sulfanylphenoxymethyl) oxyrane(1), 4.83 g (67 mmol) of acrylic acid, 0.065 g (0.3 mmol) of triethyl benzyl ammonium chloride (TEBAC), and hydroquinone crystals were put into a 50-mL two-necked flask. This mixture was heated at 90° C. for 3 hours, cooled, and then diluted with 50 mL of methylene chloride. The resulting solution was washed with water, its pH adjusted to pH 7, and then dried with $CaCl_2$. Next, the solvent was removed with a vacuum rotary evaporator without heating, thereby obtaining a residue (16.7 g). The resulting residue was identified as DDDA (or 2-hydroxy-3-[4-({4-[2-hydroxy-3-(prop-2-enoyloxy)-propoxy]phenyl}sulfanyl)phenoxy]-propyl-prop-2-enoate).

Synthesis Example 3: DDTA Monomer

A solution of 8.2 mL (9.1 g, 100 mmol) of acryloyl chloride dissolved in 25 mL of $CH_2Cl_2$ was added dropwise to a mixed solution including 16.70 g (35.5 mmol) of DDDA (or 2-hydroxy-3-[4-({4-[2-hydroxy-3-(prop-2-enoyloxy)-propoxy]phenyl}sulfanyl)phenoxy]-propyl-prop-2-enoate) and a solution of 9.45 mL (12.8 g, 126 mmol) of triethyl-amine (TEA) dissolved in 50 mL of dry $CH_2Cl_2$, while cooling (at a bath temperature of 0-5° C.) and stirring. After stopping the cooling, the resulting mixture was stirred at room temperature for about 4 hours, and 100 mL of chloroform was added thereto, followed by separation of an organic phase, washing of the organic phase with water, and drying of the organic phase with $CaCl_2$. The solvent was removed with a vacuum rotary evaporator without heating. The resulting residue (viscous oil, 20.3 g) was dissolved in benzene and purified by column chromatography (stationary phase: $SiO_2$, eluent: benzene), thereby obtaining a wide light yellow fraction. Next, the benzene was removed to recover DDTA (or 1-[4-({4-[2,3-bis(prop-2-enoyloxy)propoxy]phenyl}-sulfanyl)-phenoxy]-3-(prop-2-enoyloxy)propan-2-yl-prop-2-enoate) as yellow viscous oil with a yield of about 13.2 g (65%). [1H NMR ($CDCl_3$): 4.14 (d, 4H, 2CH2), 4.43 (2H) and 4.51 (2H)—AB-system (2CH$_2$), 5.46 (m, 2H, 2CH), 5.85 (m, 4H), 6.12 (m, 4H), 6.41 (m, 4H)-ABC-system (four acryloyl groups), 6.82 (4H$_{arom}$), 7.24 (4H$_{arom}$). Found: m/z 582.1556 [M+]. $C_{30}H_{30}N_{10}S$. Calculated: M=582.1554.]

Synthesis Example 4: N-Acryloylthiomorpholine Monomer

N-acryloylthiomorpholine was synthesized in a 500-mL, dried three-necked flask equipped with a mechanical stirrer, a thermometer, and a dropping funnel for pressure equalization. The flask was filled with 200 mL of benzol, 35 g of potassium carbonate, and 20 mL of thiomorpholine, and then cooled down to 0° C. A solution of 20 mL of acryloyl chloride in benzol (80 mL) was added dropwise into the flask at a temperature of 0-2° C. for 2 hours while the contents of the flask were stirred. The resulting reaction mixture was then stirred at 0-2° C. for 1 hour. The resulting white precipitate was filtered through a Teflon funnel with two layers of filter paper laid therein, washed three times with 50 mL of benzol each time (3×50 mL), and then squeezed, thereby obtaining an organic filtrate. The organic solvent was removed from the organic filtrate with a rotary evaporator in a reaction bath at 40-50° C. 17.7 g of the resulting raw product was distilled under a reduced pressure to obtain 13.0 g (42%) N-acryloylthiomorpholine. This product was a transparent, colorless, viscous oily liquid having good solubility in chloroform, dichloromethane, benzol, chlorinated carbon, and most organic solvents.

Synthesis Example 5: Sulfonium Derivative of Ceramidonin

After 0.8 g of $P_2O_5$ was dissolved in 4 mL of newly distilled methanesulfonic acid with stirring, 2 mmol of heptyl phenyl ether and 2 mmol of a sulfoxide (Formula 5) were added to the resulting mixture.

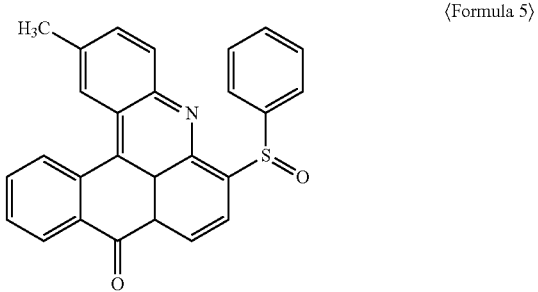 [SMILES: Cc1ccc2c(c1)=C1c3ccccc3C(=O)C3C=CC(S(=O)c4ccccc4)=C(N=2)C13]

⟨Formula 5⟩

After the mixture was stirred for 3 hours, a solution of 3 mmol of $KPF_6$ in 10 mL of water was added to the mixture and stirred for 30 minutes. After a tarry precipitate was separated and dissolved in dichloromethane, the resultant organic phase was washed with a solution of $KPF_6$ in water and then with water, dried over $Na_2SO_4$, and then evaporated to reduce the volume. After adding ethyl ether to the resulting product to separate a salt (Formula 6), its reprecipitation from dichloromethane using ethyl ether was performed once more.

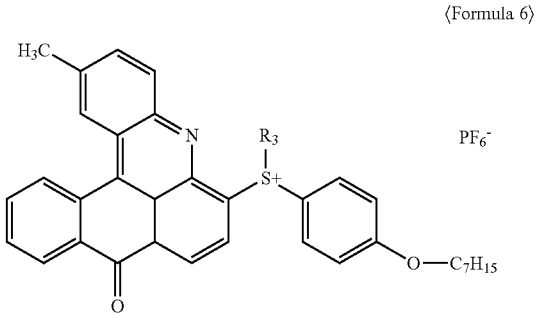

⟨Formula 6⟩

Examples 1 to 3: Preparation of Photopolymer Composition

Photopolymer compositions having the compositions shown in Table 1 were prepared. All the components in each photopolymer composition were thoroughly mixed using a mechanical stirrer and an ultrasonic bath.

TABLE 1

| Component | Example 1 | Example 2 | Example 3 |
|---|---|---|---|
| Binder resin | 60 mg of polyvinylacetate | 60 mg of polyvinylacetate | 60 mg of polyvinylacetate |
| Monomer | 10 mg of DDTA of Synthesis Example 3 | 10 mg of DDDA of Synthesis Example 2 | 10 mg of DDDO of Synthesis Example 1 |
| Cross-linkable monomer | 1,4-bis(acryloyl)piperazine 13 mg | 1,4-bis(acryloyl)piperazine 13 mg | 1,4-bis(acryloyl)piperazine 13 mg |
| Photosensitive dye | 0.025 mg of sulfonium derivative of ceramidonin of Synthesis Example 5 | 0.025 mg of sulfonium derivative of ceramidonin of Synthesis Example 5 | 0.025 mg of sulfonium derivative of ceramidonin of Synthesis Example 5 |
| Co-initiator | 10 mg of tetrabutylammonium butyltriphenylborate | 10 mg of tetrabutylammonium butyltriphenylborate | 10 mg of tetrabutylammonium Butyltriphenylborate |
| Co-initiator | 8 mg of 5-methyl-1,3,4-thiadiazole-2-thiol | 8 mg of 5-methyl-1,3,4-thiadiazole-2-thiol | 8 mg of 5-methyl-1,3,4-thiadiazole-2-thiol |
| Solvent | 200 mg of chloroform | 200 mg of chloroform | 200 mg of chloroform |

Examples 4 to 6: Preparation of Holographic Recording Medium

Holographic recording media of Examples 4 to 6 were prepared using the photopolymer compositions of Examples 1 to 3, respectively. First, 650 mL of each of the photopolymer compositions were poured onto a microscope slide (76 mm×26 mm×1 mm), covered with a Petri dish to reach an optimal vapor concentration of solvent above a surface of the photopolymer layer, and then left to dry under the Petri dish at 23-26° C. and at a humidity of 50% or less for 18 to 20 hours. As a result of the drying, a photopolymer layer having a thickness of about 40-45 µm was formed. This photopolymer layer was covered with a Mylar® protective film.

Comparative Example 1: Preparation of Photopolymer Composition

A photopolymer composition having the composition shown in Table 2 was prepared. All the components were thoroughly mixed using a mechanical stirrer and an ultrasonic bath.

TABLE 2

| Component | Comparative Example 1 |
|---|---|
| Binder resin | 60 mg of polyvinylacetate |
| Monomer | 10 mg of N-acryloylthiomorpholine of Synthesis Example 4 |
| Cross-linkable monomer | 13 mg of 1,4-bis(acryloyl)piperazine |
| Photosensitive dye | 0.025 mg of sulfonium derivative of ceramidonin of Synthesis Example 5 |
| Co-initiator | 10 mg of tetrabutylammonium butyltriphenylborate |
| Co-initiator | 8 mg of 5-methyl-1,3,4-thiadiazole-2-thiol |
| Solvent | 200 mg of chloroform |

Comparative Example 2: Preparation of Holographic Recording Medium

A holographic recording medium of Comparative Example 2 was prepared using the photopolymer composition of Comparative Example 1. First, 650 mL of the photopolymer composition was poured onto a microscope slide (76 mm×26 mm×1 mm), covered with a Petri dish to reach an optimal vapor concentration of solvent above a surface of the photopolymer layer, and then left to dry under the Petri dish at 23-26° C. and at a humidity of 50% or less for 18 to 20 hours. As a result of the drying, a photopolymer layer having a thickness of 40 µm was formed. This photopolymer layer was covered with a Mylar® protective film.

<Evaluation Results>

Recording of Hologram

Figure 2:
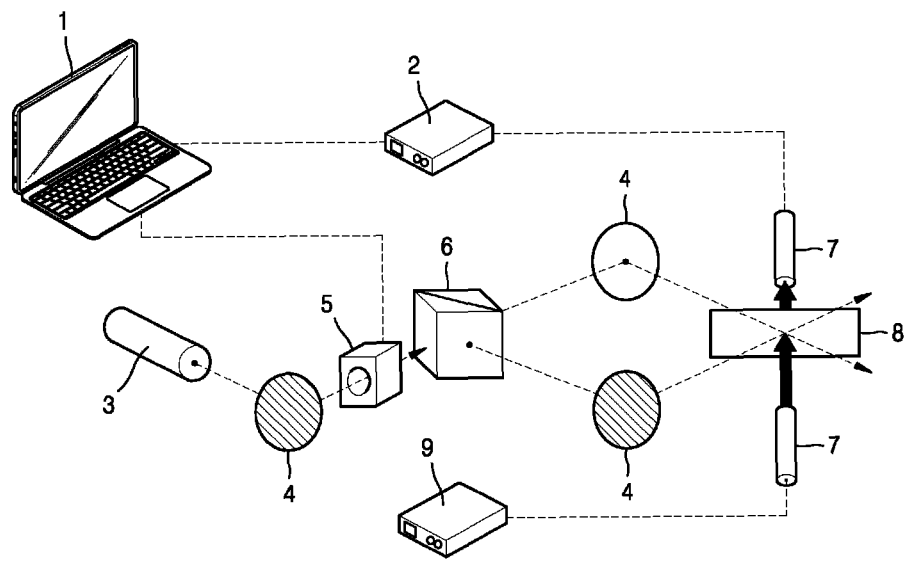
FIG. 2 is a diagram illustrating a holographic recording apparatus.

Holograms were recorded on the holographic recording media of Examples 4 to 6 and Comparative Example 2 with a holographic recording apparatus as illustrated in FIG. 2. Referring to FIG. 2, the holographic recording apparatus may include a computer 1, a spectrometer 2 (Avantes AvaSpec-2048), a blue diode-pumped solid state (DPSS) laser 3, a mirror 4, a shutter 5, a beam splitter 6, an optical fiber 7, a photopolymer layer 8, and a light source 9. The photopolymer layer of each of the holographic recording media was evaluated through phase reflection hologram recording. The phase reflection holograms were recorded using two beams traveling in opposite directions, wherein a signal beam was perpendicularly incident onto a surface of the photopolymer layer, and a reference beam was incident onto a rear surface of the photopolymer layer at an angle of 57°. A blue DPSS laser (473 nm) was used, and the total power of the laser beam was 10 mW/cm$^2$, which was measured using a LaserCheck power meter (Coherent Inc.). The spatial frequency of the holographic gratings was about 6,000 line/mm at a wavelength of 473 nm. The hologram diameter was 10 mm, and the holographic recording time was 20 seconds. During the experiment with the holographic recording apparatus of FIG. 2, arrays of transparent spectra were recorded in real time.

Diffraction Efficiency Measurement

Diffraction efficiencies (DE) were evaluated using spectrophotometry as described in W. K. Smothers, B. M. Monroe, A. M. Weber, D. E. Keys, "Photopolymers for Holography," Proc. SPIE 1212, 20-29 (1990), the entire contents of which are incorporated herein by reference.

$$DE = (1 - T_p/T_0) \times 100\%$$

wherein $T_p$ is the hologram transmittance at a playback wavelength, and $T_0$ is the sample transmittance at a playback wavelength with no hologram being recorded.

The sensitivity was evaluated as the exposure energy required for the DE to reach 0.9 from the maximum DE.

Shrinkage Test

Shrinkage of a photopolymer affects the characteristics of volume transmission and reflection holographic gratings. In the present disclosure, physical (geometric) shrinkage of the thickness of the photopolymer layer is distinguished from effective shrinkage. Effective shrinkage reflects both a thickness change and a refractive index of the photopolymer layer, and represents a change in length of the path of light passing through holographic gratings. A shrinkage measurement was directly performed during a holographic recording process to avoid the effects of a contact method or external exposure (other than exposure for hologram recording). Additional measurements, such as measurements of refraction characteristics and spectrum characteristics, were performed without removing the holographic recording medium from the experimental apparatus, after the holographic recording process was finished.

Figure 3:
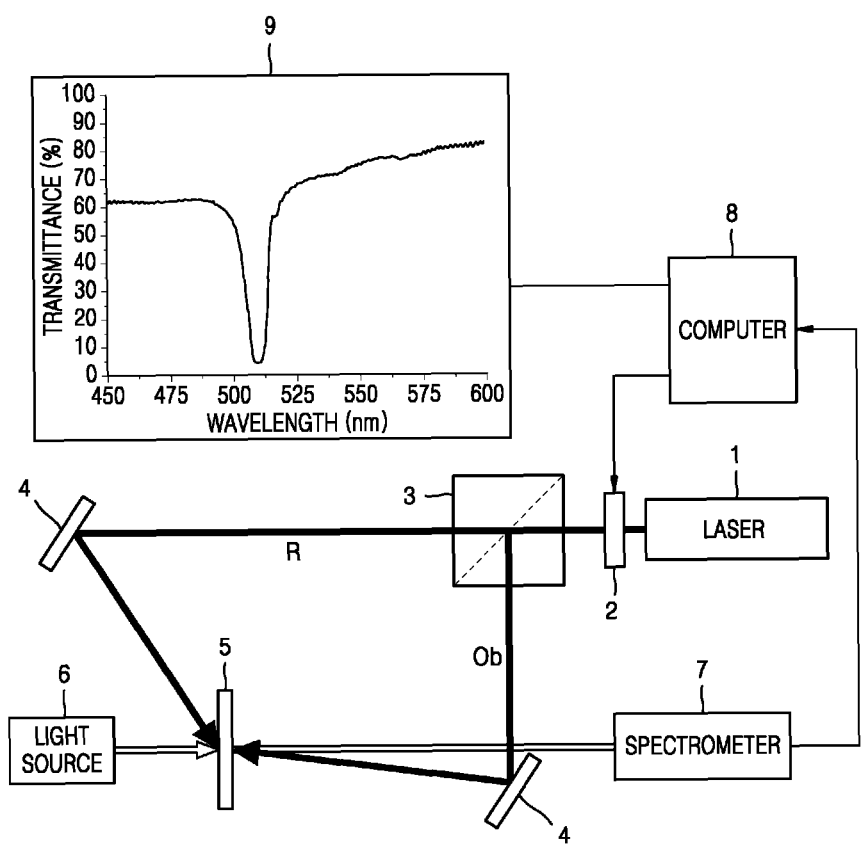
FIG. 3 is a diagram illustrating a shrinkage measurement apparatus.

The shrinkage measurement was performed using a shrinkage measurement apparatus of FIG. 3. Referring to FIG. 3, the shrinkage measurement apparatus of FIG. 3 may include a laser 1, a shutter 2, a beam splitter 3, mirrors 4, a recording medium 5, a white light source 6, a spectrophotometer 7, a computer 8, and a computer display 9. As a laser beam passes through the shutter 2, an object beam Ob and a reference beam R may be generated by the beam splitter 3 and guided by the mirrors 4 to opposite surfaces of the same region of the photopolymer layer of the recording medium 5 at different incident angles, respectively. The interference of the beams (Ob and R) may generate volume reflection holograms. Low-intensity white light as probing light may be perpendicularly incident onto a surface of the photopolymer layer and then travel toward the photospectrometer 7 after passing through the photopolymer layer of the recording medium 5. A result of a spectral response may be observed on a screen of the computer display 9. The transmission spectra of generated holograms were measured simultaneously with the start of exposure and periodically during the holographic recording process.

Shrinkage Determination

Figure 4A:
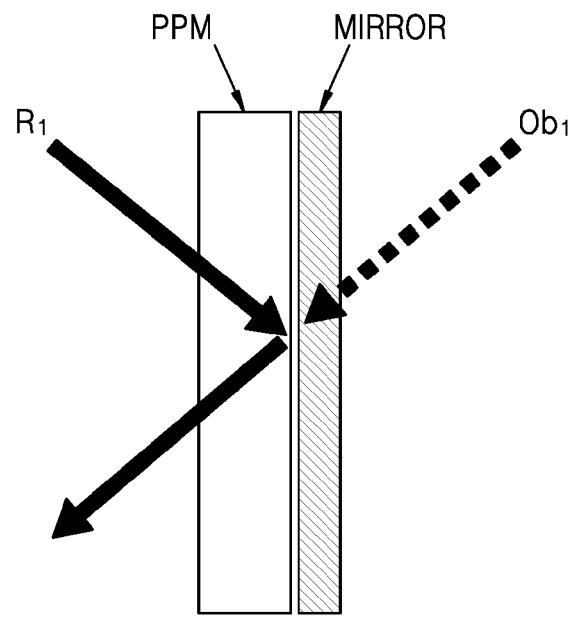
FIGS. 4A and 4B are a diagrams illustrating an object beam, a reference beam, a probing beam, and a volume reflection hologram.
Figure 4B:
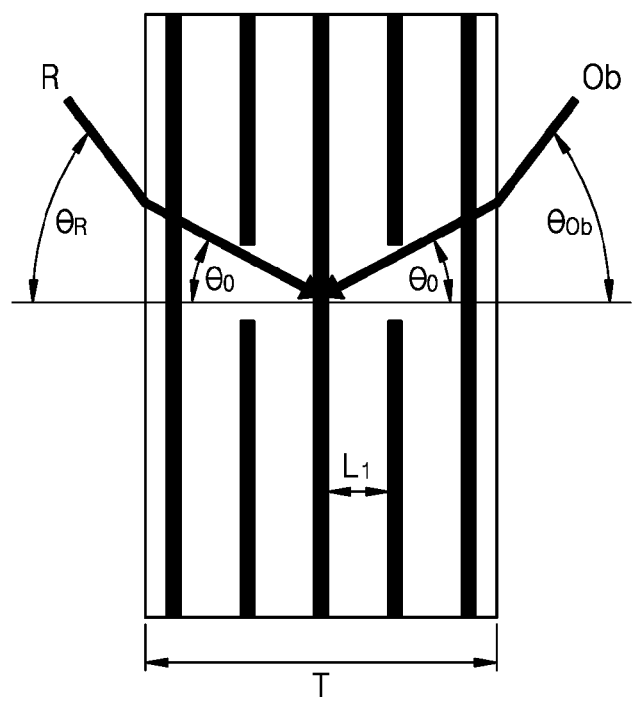
Figure 5:
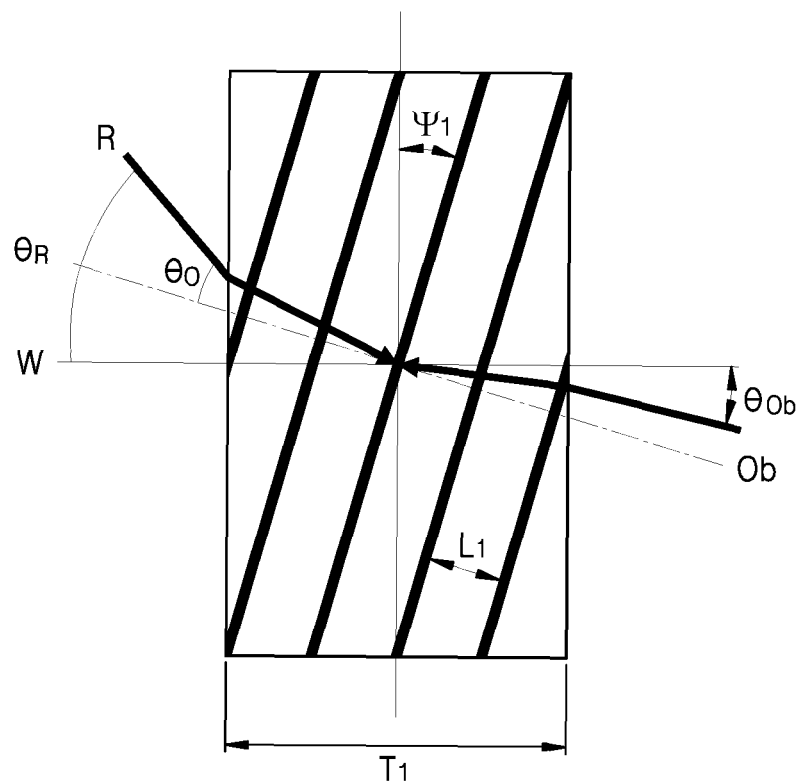
FIG. 5 is a diagram illustrating $\psi_1$, the angle of the grating vector with respect to the direction of the white light probing beam direction W and the surface of the photopolymer.

As the incident angles of the reference beam R and the object beam Ob are asymmetric to each other, the angle of the grating vector with respect to the direction of the white light probing beam direction W and the surface of the photopolymer may be represented as $\psi_1$ (see FIG. 5). FIGS. 4A and 4B are a diagram illustrating an object beam, a reference beam, a probing beam, and a volume reflection hologram, wherein the following relations may be satisfied.

$$\theta_0 = \frac{1}{2}[\sin^{0-1}((\sin\theta_R)/n_1) + \sin^{-1}((\sin\theta_{Ob})/n_1)]$$

$$\psi_1 = \frac{1}{2}[\sin^{-1}((\sin\theta_R)/n_1) - \sin^{-1}((\sin\theta_{Ob})/n_1)],$$

$$L_1 = \frac{\lambda_1}{2n_1\cos\theta_0},$$

A wavelength of the spectral response at the start of holographic recording may be represented by $$\lambda_{r\_start} = \frac{\lambda_1 \cos\psi_1}{\cos\theta_0}.$$

A value of $\lambda_{r\_start}$ may differ from that of the wavelength of recording light due to the constitution of an object beam, a reference beam, and a probing beam.

As described above, the average refractive index and the average thickness of the photopolymer layer change during the holographic recording.

Accordingly, holographic grating parameters may be varied as follows.

$$\psi_2 = tg^{-1}(Stg\psi_1), \; L_2 = L_1 \frac{\sin\psi_2}{\sin\psi_1} = \frac{\lambda_1 \sin(tg^{-1}(Stg\psi_1))}{2n_1\cos\theta_0\sin\psi_1}$$

The wavelength of the spectral response of holographic gratings upon finishing of the holographic recording may be represented by $$\lambda_{r\_finish} = \frac{n_2\lambda_1\sin2\psi_2}{2n_1\cos\theta_0\sin\psi_1}.$$

Effective shrinkage may be defined as follows.

$$S_{effective} = \frac{\lambda_{r\_finish}}{\lambda_{r\_start}}$$

Effective shrinkage may represent a change in the relative optical path moving along the grating vector, and reflect both a reduced thickness of the photopolymer layer (this may lead to a shift to a shorter wavelength in the spectral response of a reflection hologram) and an increased average refractive index of the photopolymer layer (this may lead to an opposite effect from that from the reduced thickness).

The results of measuring the diffraction efficiency, sensitivity, and shrinkage of the photopolymer layer of each of the holographic recording media of Examples 4 to 6 and Comparative Example 2 are shown in Table 3.

TABLE 3

| Sample | Diffraction efficiency (%) | Sensitivity (mJ/cm²) | Sh$_{bp}$ (%) | Sh$_{ap}$ (%) |
|---|---|---|---|---|
| Example 1 | 80 | 15 | 1.2 | 2.0 |
| Example 2 | 80 | 20 | 1.3 | 2.6 |
| Example 3 | 75 | 50 | 0.12 | 0.13 |
| Comparative Example 2 | 65 | 5 | 2.3 | 2.9 |

It should be understood that exemplary embodiments described herein should be considered as being descriptive only and do not limit the present disclosure. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present disclosure as defined by the following claims.

What is claimed is:

1. A photopolymer composition for holographic recording, the photopolymer composition comprising a photosensitive dye, a co-initiator, a monomer, a cross-linkable monomer, a binder resin, and a solvent, wherein the monomer comprises

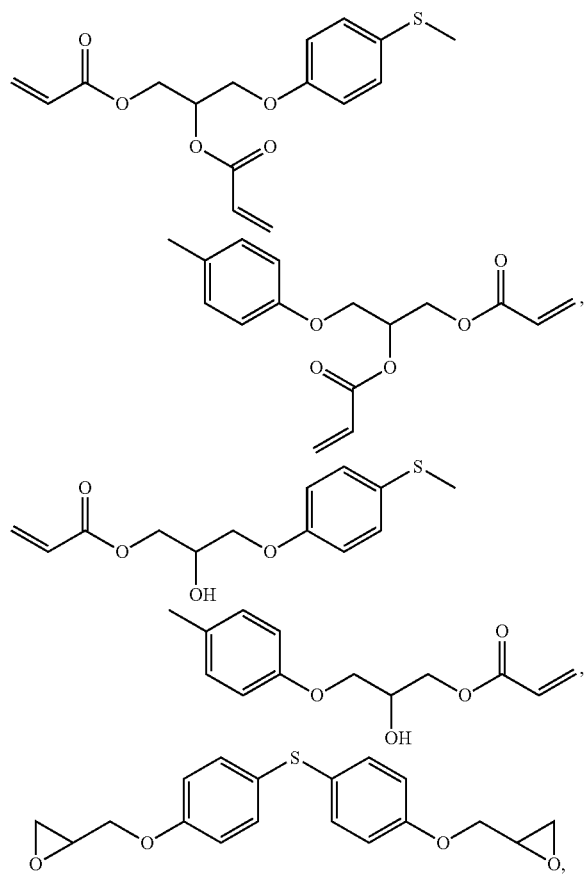

or a combination thereof,
wherein the photosensitive dye comprises a sulfonium derivative of ceramidonin.

2. A holographic recording medium comprising a substrate, a photopolymer layer, and a protective layer, wherein the photopolymer layer comprises the photopolymer composition according to claim 1.

3. The photopolymer composition according to claim 1, wherein the sensitivity of the photopolymer composition is between 15 and 50 mJ/cm².

4. The photopolymer composition according to claim 3, exhibiting a shrinkage of between 0.12% and 1.3%.

5. A photosensitive dye comprising a sulfonium derivative of ceramidonin represented by:

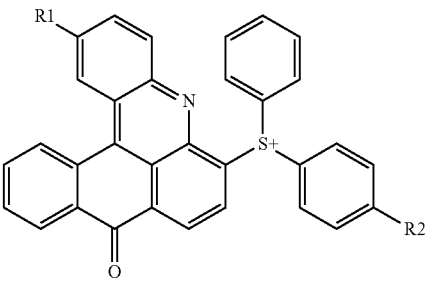

where $R_1$ and $R_2$ are each independently a hydrogen atom, a halogen atom, a $C_1$-$C_5$ alkyl group, a $C_1$-$C_5$ alkoxy group, or a primary or secondary amine group having a $C_1$-$C_5$ alkyl group.

6. A photopolymer composition comprising a photosensitive dye, a co-initiator, a monomer, a cross-linkable monomer, a binder resin, and a solvent,
wherein the photosensitive dye comprises a sulfonium derivative of ceramidonin represented by:

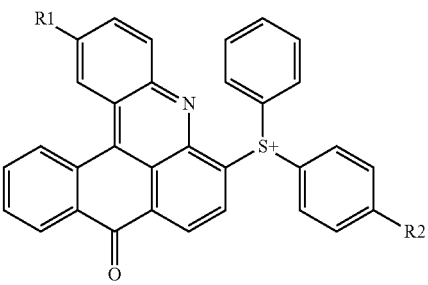

where $R_1$ and $R_2$ are each independently a hydrogen atom, a halogen atom, a $C_1$-$C_5$ alkyl group, a $C_1$-$C_5$ alkoxy group, or a primary or secondary amine group having a $C_1$-$C_5$ alkyl group.

7. The photopolymer composition of claim 6, wherein the monomer comprises

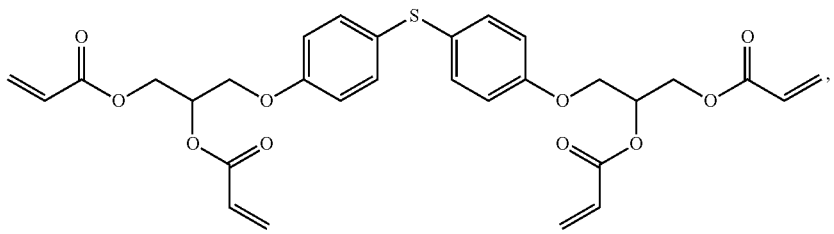 [SMILES: C=CC(=O)OCC(COc1ccc(Sc2ccc(OCC(COC(=O)C=C)OC(=O)C=C)cc2)cc1)OC(=O)C=C]

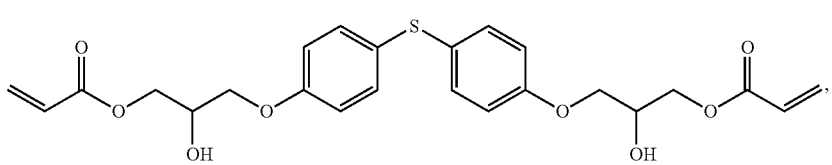

-continued

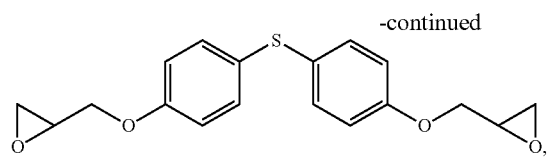

or a combination thereof.

8. The photopolymer of claim 7, wherein the monomer comprises

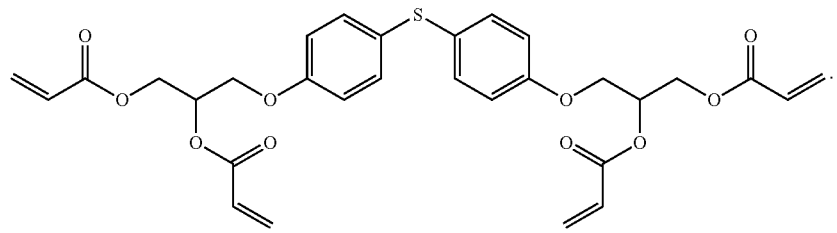

9. The photopolymer of claim 7, wherein the monomer comprises

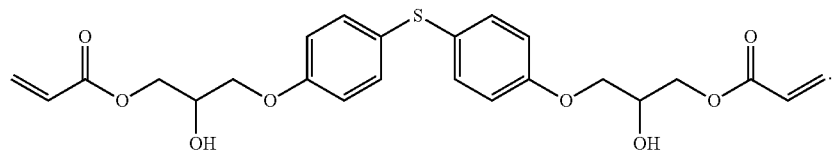 [SMILES: C=CC(=O)OCC(O)COc1ccc(Sc2ccc(OCC(O)COC(=O)C=C)cc2)cc1]

10. The photopolymer of claim 7, wherein the monomer comprises

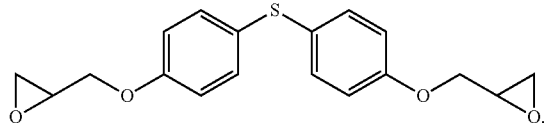 [SMILES: c1cc(Sc2ccc(OCC3CO3)cc2)ccc1OCC1CO1]

11. A holographic recording medium comprising a substrate, a photopolymer layer, and a protective layer, wherein the photopolymer layer comprises the photopolymer composition according to claim 7.

12. The photopolymer composition according to claim 7, wherein the sensitivity of the photopolymer composition is between 15 and 50 mJ/cm$^2$.

13. The photopolymer composition according to claim 12, exhibiting a shrinkage of between 0.12% and 1.3%.

14. A holographic recording medium comprising a substrate, a photopolymer layer, and a protective layer, wherein the photopolymer layer comprises the photopolymer composition according to claim 6.

* * * * *